United States Patent
Lu et al.

(10) Patent No.: US 7,049,157 B2
(45) Date of Patent: May 23, 2006

(54) CALIBRATION STANDARD FOR CRITICAL DIMENSION VERIFICATION OF SUB-TENTH MICRON INTEGRATED CIRCUIT TECHNOLOGY

(75) Inventors: Yu-Hui Lu, Hsin-Chu (TW); Tien-Chi Wu, Yonghe (TW)

(73) Assignee: Taiwan Semiconductor Manufacturing Co., Ltd., Hsinchu (TW)

( * ) Notice: Subject to any disclaimer, the term of this patent is extended or adjusted under 35 U.S.C. 154(b) by 166 days.

(21) Appl. No.: 10/798,558

(22) Filed: Mar. 11, 2004

(65) Prior Publication Data

US 2005/0202675 A1    Sep. 15, 2005

(51) Int. Cl.
  *H01L 21/76* (2006.01)
  *H01L 23/58* (2006.01)
(52) U.S. Cl. .......................... 438/18; 438/34; 438/36; 257/48
(58) Field of Classification Search .................. 438/18, 438/22–25, 29, 31, 34–36, 484, 538, 688, 438/14; 257/48
See application file for complete search history.

(56) References Cited

U.S. PATENT DOCUMENTS

| | | | |
|---|---|---|---|
| 3,988,564 A | 10/1976 | Garvin et al. | 219/121 EM |
| 4,457,803 A | 7/1984 | Takigawa | 156/626 |
| 5,504,340 A * | 4/1996 | Mizumura et al. | 250/492.21 |
| 5,616,921 A | 4/1997 | Talbot et al. | 250/307 |
| 5,683,547 A | 11/1997 | Azuma et al. | 156/643.1 |
| 5,945,677 A | 8/1999 | Leung et al. | 250/396 R |
| 6,514,866 B1 | 2/2003 | Russell et al. | 438/712 |
| 6,528,818 B1 | 3/2003 | Satya et al. | 257/48 |
| 6,538,844 B1 | 3/2003 | Takano et al. | 360/122 |
| 2003/0049938 A1 * | 3/2003 | Lai et al. | 438/745 |
| 2004/0121531 A1 * | 6/2004 | Wieczorek et al. | 438/197 |
| 2004/0201858 A1 * | 10/2004 | Broermann et al. | 356/625 |
| 2005/0148104 A1 * | 7/2005 | Kota et al. | 438/14 |

* cited by examiner

*Primary Examiner*—Michael Lebentritt
*Assistant Examiner*—Mohsen Ahmadi
(74) *Attorney, Agent, or Firm*—Thomas, Kayden, Horstemeyer & Risley

(57) ABSTRACT

A critical dimension control wafer for calibrating process control scanning electron microscopes is described. The test wafer provides one or more test structures each consisting of an array of parallel trenches precision micro-machined in a metal plate. The trenches are formed, preferably in an aluminum/copper alloy plate, using focused ion beam milling. The micro-machined trenches have lower width roughness and lower edge roughness compared to similar patterns form in polysilicon by conventional photo lithographic methods. In addition, electron charging in the scanning electron microscope, which produces distorted images, is essentially eliminated. The dimensions of the trenches and the metal lines between them have dimensions comparable to those of polysilicon lines used in sub-tenth micron integrated circuit process technology control wafer. The control wafers are calibrated using a calibrated laboratory grade scanning electron microscope. Once calibrated, the control wafers may be stock-piled for subsequent routine use as a high precision dimensional reference, in particular for calibrating and monitoring the stability of process line scanning electron microscopes.

18 Claims, 2 Drawing Sheets

CALIBRATION STANDARD FOR CRITICAL DIMENSION VERIFICATION OF SUB-TENTH MICRON INTEGRATED CIRCUIT TECHNOLOGY

BACKGROUND OF THE INVENTION (1) Field of the Invention

This invention relates to testing and diagnostics of line processes used for the manufacture of integrated circuit devices and more particularly to critical dimensional measurement of sub-tenth micron pattern features during wafer processing.

(2) Description of Prior Art

The manufacture of large scale integrated circuits in a mass production facility involves hundreds of discrete processing steps beginning with the introduction of blank semiconductor wafers at one end and recovering the completed chips at the other. The manufacturing process is usually conceived as consisting of the segment wherein the semiconductor devices are formed within the silicon surface (front-end-of-line) and the portion which includes the formation of the various layers of interconnection metallurgy above the silicon surface (back-end-of-line). Most of these processing steps involve depositing layers of material, patterning them by photolithographic techniques, and etching away the unwanted portions. The materials consist primarily of insulators and metal alloys. In some instances the patterned layers serve as temporary protective masks. In others they are the functional components of the integrated circuit chip.

In order to monitor the integrated circuit manufacturing process, test structures, representative of the circuit elements are typically incorporated in regions of the wafer outside the integrated circuit chips. Examples of these in-line test devices are a dumb-bell structure testable with a four point probe to establish proper resistivity of a deposited layer, or long serpentine metal lines which can be tested to establish the presence of particulate defects by testing for electrical opens and shorts. These devices are typically designed with critical areas much larger than their corresponding elements in the integrated circuit so they are more sensitive to defects and can be tested at various stages during processing. In addition to such devices which characterize the cleanliness and integrity of the process line, tests sites must also be provided which can characterize the integrity of the pattern alignment and its planar dimensions. For this it is desirable to have a means of providing features which are not produced by the same process which produces the pattern. In other words, it would be desirable to have structures by which the can provide a dimensional and alignment reference for evaluating the patterning process. Of particular interest in this application is the ability to accurately measure and characterize the planar integrity of polysilicon lines which are patterned in a deposited polysilicon layer by plasma etching. For this purpose CD (critical dimension) control wafers are used. In present technology, the control wafers are prepared with a polysilicon layer into which lines have been patterned using conventional photolithography and etching. The lines are then calibrated by measurement with a laboratory standard scanning electron microscope (SEM). The calibrated CD control wafer is then used to calibrate and monitor the line SEMs which are routinely used for quality control by the integrated circuit manufacturing line. The line SEMs are used to monitor and verify the critical dimensions of features on and product wafers.

Optical photolithography has been the preferred method for patterning features on integrated circuits for many decades. While its limitations have often been wrongly anticipated for years as integrated circuit technology advanced to smaller and smaller dimensions, optical photolithography has nevertheless managed to keep in step and remain the most cost effective and reliable patterning process. At present, device dimensions are at the sub tenth micron level and are expected to continue to shrink in the future. The desired dimensional and alignment reference structures mentioned supra must therefore be formed by a non-photolithographic process.

Unfortunately, polysilicon lines patterned by these conventional photolithographic and etching processes, which are the essentially the same as those used to manufacture the IC product, suffer from a number of problems which compromise their desirability as calibration standards. These problems include edge roughness and poor dimensional uniformity. In addition, because the lines are of polysilicon, they tend to become charged during the SEM measurement resulting in serious image distortion. It would therefore be desirable to have a critical dimension calibration standard for manufacturing SEMs which includes SEM measurable features which have dimensional parameters comparable to the IC product but without the shortcomings of those formed by the manufacturing processes of the IC product. For example the problem of charging during SEM measurement would be greatly reduced if not entirely eliminated if the calibration feature (lines) on the SEM calibration wafer were made of a material more conductive than polysilicon, such as aluminum or gold. Similarly, the problems of edge roughness and uniformity could be overcome on the calibration wafer by forming the line by a process other than photolithography and etching. These problems are addressed and overcome by the teaching of the present invention.

Focused ion beams have been used for years to thin or remove layers using a hardmask or a photoresist mask. An early example of this form of micro machining or milling using a focused ion beam is cited as early as 1976 by Garvin, et. al., U.S. Pat. No. 3,988,564. Progress was relatively slow with regard to patterning with a focused ion beam (FIB) slow because, like electron beam patterning, it took a relatively long time to pattern photoresist on a wafer by scanning a single beam. This became even more impractical as wafer size increased from about 75 mm. to the present day 150 mm. wafer. Furthermore, FIB systems could not bring about high ion currents at small spot size. More recently Leung, et. al., U.S. Pat. No. 5,945,667 cited an improved ion beam system which overcome these problems. Nevertheless, full wafer patterning of today's large wafers with a single FIB is still not practical. However, FIB technology, particularly, now with greatly improved small spot size and high ion currents, is found by the present inventors, to be useful as well as practical for providing independent reliable test structures for critical dimension measurements and SEM calibration in the sub tenth micron process technology.

Russell, et. al., U.S. Pat. No. 6,514,866 B2 shows a method for micro machining a copper film with a focused beam of gallium Ions while the film is in an ambient of organic chloride or organic hydroxide vapor. The gallium ions selectively sputter the copper, producing a rough surface thereon, while neighboring material, such as a dielectric is not removed. In another similar application, Takigawa, U.S. Pat. No. 4,457,803 uses a focused beam of argon ions to selectively sputter an oxide film.

Azuma, et. al., U.S. Pat. No. 5,683,547 shows a method for using a focused energy beam such as an ion beam to assist the local etching of a material with an etchant gas. Satya, et. al., U.S. Pat. No. 6,528,818 shows a method for scanning a region on a wafer for defects using a charged particle beam. Takano, et. al., U.S. Pat. No. 6,538,844 B2 shows a method for fabricating a magnetic head by focused ion beam etching while Talbot, et. al., U.S. Pat. No. 5,616,921 shows a method for controlling preferential etching during focused ion milling by using a mask image.

SUMMARY OF THE INVENTION

It is an object of this invention to disclose a test structure having multiple metal lines separated from each other by precision micro-machined trenches formed on a control wafer which can be used as a high precision dimensional reference, in particular as applied to the calibration and monitoring the stability of SEMs used for monitoring sub tenth-micron integrated circuit process technology.

It is a another object of this invention to provide a method for forming precision trenches in a metal layer with low width roughness, low edge roughness, and with reduced charging.

It is yet another object of this invention to provide a method for forming a reference test structure having multiple precision trenches which can be used as dimensional references for the in-line characterization of polysilicon lines after said lines are patterned.

It is still another object of this invention to provide a method for forming precision trenches in a metal layer on a substrate, said trenches having a width of between about 30 and 90 nm. and a width uniformity 3-sigma of between about 3.0 and 3.5 nm.

It is yet another object of this invention to provide a method for forming precision trenches in a metal layer on a substrate, said trenches having a width of and a mean value of width roughness of between about 3.0 and 3.7 nm. and a mean value of edge roughness of between about 1.8 and 2.2 nm.

These objects are accomplished by depositing a metal film comprising an aluminum copper (AlCu) alloy onto a substrate and then forming trenches in the AlCu alloy with a focused ion beam.

It is another object of this invention to provide a method for forming a CD (critical dimension) control wafer and calibration standard, having test structures consisting of precision trenches in a metal layer having a width of about 45 nm. and a width uniformity 3 sigma of between about 3.0 and 3.5 nm.

It is still another object of this invention to provide a method for forming a CD control wafer, having structures consisting of precision trenches in a metal layer having mean values of width roughness of between about 3.0 and 3.7 nm. and mean values of edge roughness of between about 1.8 and 2.2 nm.

These objects are accomplished by depositing a metal film comprising an aluminum and copper (AlCu) alloy onto a wafer and micro-machining trenches in the AlCu alloy with a focused ion beam.

DESCRIPTION OF THE PREFERRED EMBODIMENTS

In an embodiment of this invention an SEM calibration pattern will be formed on a silicon wafer. The calibration pattern consists of a set of parallel trenches dug into a metal layer using a focused ion beam. The widths of the trenches will be of the order of 50 nm. The widths of the metal lines which separate the trenches is arbitrary and may typically exceed 500 nm. The widths of the trenches and metal lines are verified by measurement in a laboratory calibrated SEM. After calibration, the wafer is used in a manufacturing environment as reference for calibration of SEMs, used to monitor critical dimensions of integrated circuit product flowing through a process line. The wafer may also used to verify and monitor the stability of the SEMs.

Figure 1:
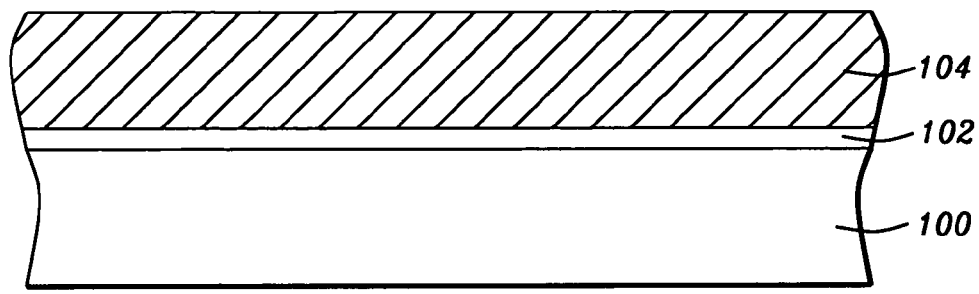
FIG. 1 and FIG. 2 are cross sections of a wafer illustrating the process steps for forming a critical dimension control wafer according to an embodiment of this invention.

Referring to FIG. 1, a silicon wafer 100 is provided. A thin silicon oxide pad layer 102, between about 50 and 200 nm. thick is thermally grown on the wafer 100 by conventional thermal oxidation. The pad oxide layer 102 serves as a stress buffer and adhesion layer for a metal layer 104 which is next deposited onto the wafer 100, preferably by vacuum evaporation. The metal layer 104 preferably comprises an aluminum-copper alloy. The layer 104 is deposited to a thickness of between about 400 and 1000 nm. The aluminum-copper alloy preferably contains between about 0.1 and 1.0 percent copper by weight.

Figure 2:
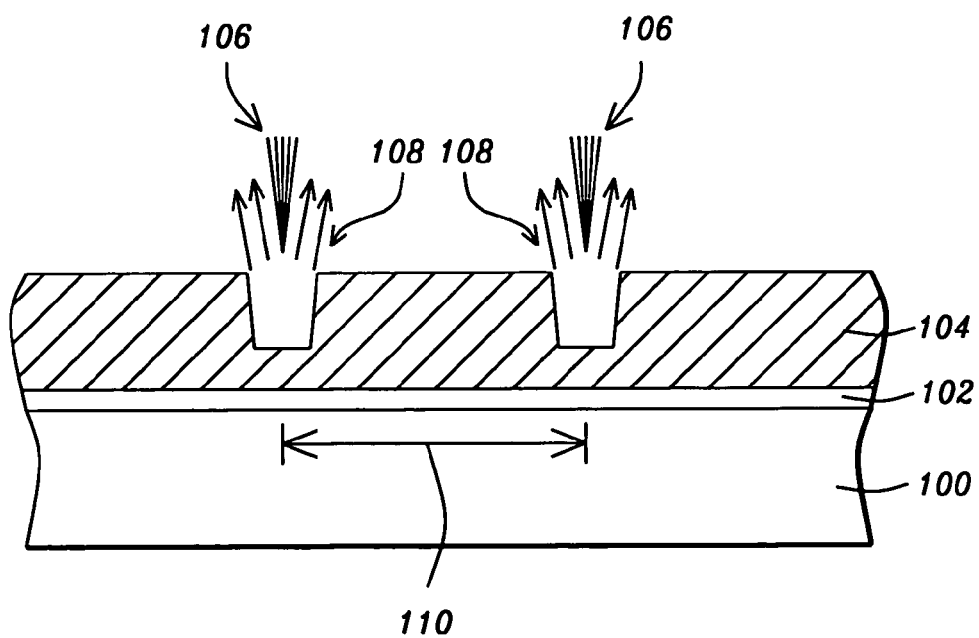

Referring now to FIG. 2, the CD control wafer 100 is mounted onto a motor driven X-Y stage of a focused ion beam processing tool. A suitable tool is the Model XL 830 manufactured by the FEI Company, 5350 NE Dawson Creek Dr. Hillsboro, Oreg. 97124 USA. After the tool is evacuated to a background pressure of between about $5\times10^{-7}$ and $2.3\times10^{-6}$ mTorr. A focused beam 106 of germanium ions is selectively directed onto the wafer while the wafer is moved under the beam 106 with the by X-Y stage. The focused ion beam 106 formed of activated germanium ions drawn out into a beam by an electric field while maintaining an operating pressure of between about $1.5\times10^{-7}$ and $1.9\times10^{-7}$ Torr. The ion beam is directed at the wafer at an ion energy of between about 25 and 35 keV and a current of between about 0.5 and 3 pA. The focused ion beam 106 gouges out linear trenches 108 in the metal layer 102. The trenches 108 are substantially parallel and are between about 50 and 500 nm. wide, and preferably between 30 and 90 nm. wide, at the surface and between about 200 and 500 nm. deep. The pitch 110 of the channels 108 is between about 100 and 600 nm. The trenches typically have mean values of width roughness of between about 3.0 and 3.7 nm. Edge roughness, which is defined as the mean variation of the edge about its linear least square average, typically has values of between about 1.8 and 2.2 nm.

Wafer 100 is next mounted in the chamber of a calibrated standards laboratory SEM and the widths of the trenches and their pitch are measured and recorded. In addition, the edge roughness is observed and measured to assure standards grade quality of the FIB gouged trenches. The CD wafer 100 is now stored and made available as a reference standard for the calibration of process line quality control SEMs which measure dimensions on product wafers as well as test site wafers passing through in the process line. A typical calibration procedure may demand a daily observation of a CD control wafer by the process SEM. The CD control wafer is mounted in the chamber of the process SEM and the recorded image is measured with reference to dimensions recorded for the CD wafer by the laboratory SEM. After calibration the CD control wafer is removed from the SEM chamber and product wafers from the process line are then measured in a series of routine SEM operations. After a pre-determine time period or after a pre-determined number of product wafer measurements, each involving mounting a product or test site wafer in the SEM chamber, pumping the chamber down, operating the SEM to obtain a measurable image, and then removing the product/test site wafer.

The frequency of calibration, of course, must be determined empirically, However, a single calibrated CD control wafer may be used over and over again to calibrate the process SEM. Because the pattern on the CD control wafer is formed on a highly conductive metal, the pattern is not subject to charging in the SEM. This greatly extends the life of the control wafer.

Figure 3:
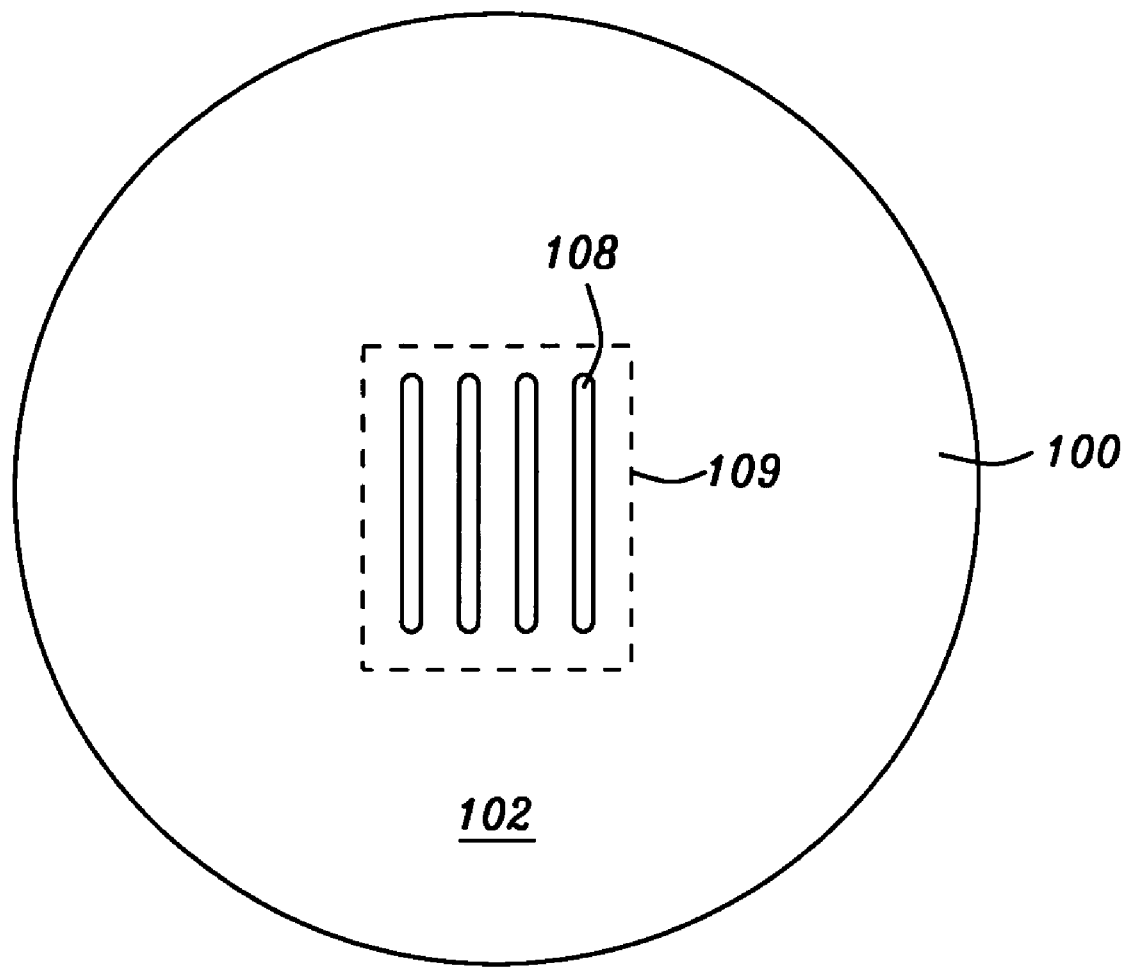
FIG. 3 is a planar view of a wafer having an array of parallel trenches formed in a metal plate according to the embodiment of this invention.

In FIG. 3, there is shown a planar view of a CD control wafer 100. In this illustration a single array of trenches 108 have been formed in a metal layer 102 which covers the entire surface of the wafer. Alternately, the metal layer 102 may itself be patterned, prior to the formation of the trenches. Such a pattern could be a metal region 109 just around the trench array. A smaller pattern such as the region 109 would make the trench pattern easier to find in the SEM. The metal region 109 is preferably rectangular and between about 5 and 50 µm. on a side with the trench array covering a region of about 4×10 µm. It is also advantageous to include several different trench widths in the array in order to test the linearity of the process control SEM.

While the embodiment utilizes an CD control wafer to measure and verify the dimensions of a polysilicon gate electrode, it should be understood that the CD control wafer, as described and claimed in the present invention could easily and effectively be used to verify critical dimensions of other patterned features, for example metal interconnect lines or additional higher level polysilicon lines.

What is claimed is:

1. A method for process control in an integrated circuit process comprising:
   providing a water substrate;
   forming a pad layer on said wafer substrate;
   forming a metal layer on said pad layer;
   patterning said metal layer to form at least one metal plate in at least one region of said wafer substrate;
   milling a plurality of substantially parallel trenches in said at least one metal plate, thereby forming a critical dimension test array wafer; and
   measuring the widths of said parallel trenches therebetween, thereby calibrating said critical dimension test array wafer;
   mounting and inserting said calibrated critical dimension test array wafer in a sample chamber of a process control scanning electron microscope;
   calibrating said process control scanning electron microscope by measuring the widths of said trenches therebetween; and
   using said process control scanning electron microscope to measure widths of lines on an in-process integrated circuit wafer.

2. The method of claim 1 wherein said pad layer is silicon oxide thermally grown to a thickness of between about 50 and 200 nm.

3. The method of claim 1 wherein said metal layer is between about 400 and 1,000 nm thick.

4. The method of claim 1 wherein said metal layer is an alloy of aluminum and copper wherein the copper content is between about 0.1 and 1.0 percent by weight.

5. The method of claim 1 wherein said trenches are between about 30 and 90 nm wide and have a width uniformity 3-sigma of between 3.0 and 3.5 nm.

6. The method of claim 1 wherein said trenches have a mean value of width roughness of between about 3.0 and 3.7 nm and a mean value of edge roughness of between about 1.8 and 2.2 nm.

7. The method of claim 1 wherein said measuring is accomplished using a calibrated scanning electron microscope.

8. The method of claim 1 wherein said substantially parallel trenches are formed by a focused ion beam.

9. The method of claim 8 wherein said ion are germanium.

10. The method of claim 8 wherein said ion beam has an energy of between about 25 and 35keV and a current of between about 0.5 and 3 pA.

11. A method for process control in an integrated circuit process comprising:
    providing a wafer substrate having a plurality of substantially parallel trenches and spaces milled, in a metal plate formed over a pad layer thereby forming a critical dimension test array wafer, and the widths of said parallel trenches and the spaces therebetween being measured thereby calibrating said critical dimension test array wafer;
    mounting and inserting said calibrated critical dimension test array wafer in a sample chamber of a process control scanning electron microscope;
    calibrating said process control scanning electron microscope by measuring the widths of said trenches and the spaces therebetween; and
    using said process control scanning electron microscope to measure widths and of lines on an in-process integrated circuit wafer.

12. The method of claim 11 wherein said pad layer is silicon oxide thermally grown to a thickness of between about 50 and 200 nm.

13. The method of claim 11 wherein said metal plate is between about 400 and 1,000 nm thick.

14. The method of claim 11 wherein said metal plate is an alloy of aluminum and copper wherein the copper content is between about 0.1 and 1.0 percent by weight.

15. The method of claim 11 wherein said substantially parallel trenches are formed by a focused ion beam.

16. The method of claim 15 wherein said focused ion beam comprises germanium ions.

17. The method of claim 15 wherein said focused ion beam has an energy of between about 25 and 35keV and a current of between about 0.5 and 3 pA.

18. The method of claim 11 wherein said lines comprise polysilicon lines.

* * * * *